United States Patent
Crawford et al.

(10) Patent No.: US 6,773,419 B2
(45) Date of Patent: Aug. 10, 2004

(54) BLOOD COLLECTION SET

(76) Inventors: Jamieson William Maclean Crawford, 250 W. 105th St., Apartment 3G, New York, NY (US) 10025; Stefanie Livanos, 2509 Line Ct., Bethlehem, PA (US) 18017

( * ) Notice: Subject to any disclaimer, the term of this patent is extended or adjusted under 35 U.S.C. 154(b) by 212 days.

(21) Appl. No.: 10/054,022

(22) Filed: Nov. 13, 2001

(65) Prior Publication Data

US 2002/0103464 A1 Aug. 1, 2002

Related U.S. Application Data

(60) Provisional application No. 60/260,034, filed on Jan. 5, 2001.

(51) Int. Cl.[7] ............... A61M 5/32; A61M 5/00; A61B 5/00
(52) U.S. Cl. ............... 604/198; 604/110; 600/576
(58) Field of Search ............... 604/164.08, 110, 604/192, 197, 198; 600/576–579, 583; 128/919

(56) References Cited

U.S. PATENT DOCUMENTS

| | | | |
|---|---|---|---|
| 4,747,831 A | | 5/1988 | Kulli ............... 604/110 |
| 4,813,426 A | * | 3/1989 | Haber et al. ............... 600/576 |
| 4,813,940 A | | 3/1989 | Parry |
| 4,894,055 A | * | 1/1990 | Sudnak ............... 604/198 |
| 4,900,307 A | | 2/1990 | Kulli ............... 604/110 |
| 4,927,414 A | | 5/1990 | Kulli ............... 604/110 |
| 5,342,320 A | | 8/1994 | Cameron |
| 5,501,672 A | | 3/1996 | Firth et al. |
| 5,549,558 A | | 8/1996 | Martin |
| 5,549,571 A | | 8/1996 | Sak |
| 5,591,138 A | * | 1/1997 | Vaillancourt ............... 604/263 |
| 5,779,679 A | * | 7/1998 | Shaw ............... 604/158 |
| 5,800,400 A | | 9/1998 | Hogan |
| 5,921,964 A | | 7/1999 | Martin |
| 6,322,540 B1 | * | 11/2001 | Grabis et al. ............... 604/198 |

FOREIGN PATENT DOCUMENTS

| | | |
|---|---|---|
| EP | 0409180 A1 | 1/1991 |
| WO | WO 00/12180 | 3/1999 |
| WO | WO 99/23947 | 5/1999 |

* cited by examiner

Primary Examiner—Michael J. Hayes
(74) Attorney, Agent, or Firm—Nanette S. Thomas, Esq.; Scott J. Rittman, Esq.; Mark Lindsey

(57) ABSTRACT

An automatically shieldable blood collection set is provided. The blood collection set includes a needle assembly having a hub to which a needle cannula is fixedly attached. A safety shield is telescoped relative to the hub and the needle cannula and can be moved from a proximal position where the needle cannula is exposed to a distal position where the needle cannula is safely shielded. A spring is provided between the shield and the hub to propel the shield distally relative to the hub and into surrounding relationship with the needle cannula. A retainer is provided for releasably holding the shield in a proximal ready-to-use condition relative to the hub and the needle cannula. An actuator releases the retainer and enables the shield to be propelled by the spring. A lock may be provided for preventing inadvertent re-exposure of the needle cannula.

6 Claims, 2 Drawing Sheets

BLOOD COLLECTION SET

This application claims the benefit of provisional application 60/260,034 filed on Jan. 5, 2001.

BACKGROUND OF THE INVENTION

1. Field of the Invention

The subject invention relates to a blood collection set having a needle cannula and a shield that can be driven forwardly to safely shield the needle cannula.

2. Description of the Related Art

A prior art blood collection set includes a small diameter needle cannula having a pointed distal end and a proximal end mounted to a thermoplastic hub. Portions of the blood collection set near the hub may be provided with a pair of flexible wings. The wings can be folded into face-to-face engagement with one another to facilitate digital manipulation of the small needle cannula. The wings then can be folded away from one another and taped into face-to-face engagement with the skin of the patient near a puncture site. The prior art blood collection set further includes a flexible plastic tube that has one end connected to the hub and an opposed end connected to a fitting. The fitting can be placed in communication with a reservoir to which collected blood may be directed.

The needle cannula of the prior art blood collection set typically is shielded prior to and after use to prevent accidental sticks. Needle shields used with prior art blood collection sets have taken many forms. Typically, a prior art blood collection set is packaged with a rigid tubular cap telescoped over the needle cannula to prevent accidental sticks prior to use. This tubular cap is removed from the needle cannula immediately prior to use of the blood collection set. Most prior art blood collection sets further include a second shield that is telescoped over the needle cannula and hub. The second shield may include at least one slot through which wings of the prior art hub may extend. Thus, the medical technician who uses the prior art blood collection set will hold the wings of the needle hub in one hand and the shield in the other hand after removing the needle cannula from the patient or blood donor. The wings then are slid proximally relative to the shield, thereby drawing the needle cannula into the shield. Some prior art shields are configured to engage the wings when the needle cannula has been shielded to make a re-exposure of the needle cannula difficult.

The digital manipulation that is required to shield the used needle cannula of a prior art blood collection set creates the potential for generating the accidental needle stick that the shield is intended to avoid. In particular, it is undesirable to rely upon a shielding that requires two hands to be moved in opposite directions in proximity to the point of a used needle cannula. Accordingly, the inventors herein have recognized the desirability of providing an automatically shieldable needle cannula for a blood collection set.

SUMMARY OF THE INVENTION

The subject invention relates to a blood collection set which comprises a needle cannula having a proximal end, a pointed distal end and a lumen extending therebetween.

The blood collection set further includes a hub that may be molded from a thermoplastic material. The hub includes proximal and distal ends. The hub also has inner and outer tubes that extend between the proximal and distal ends. The inner tube includes a passage that extends continuously between the proximal and distal ends of the hub. A portion of the inner tube at the distal end of the hub is securely mounted to the proximal end of the needle cannula. Thus, the lumen through the needle cannula communicates with the passage through the hub. The inner and outer tubes are connected to one another adjacent the proximal end of the hub. However, a cylindrical space exists at other locations between the inner and outer tubes and is open from the distal end of the hub. The outer tube includes an aperture extending therethrough and into the cylindrical space between the inner and outer tubes at a location near the proximal end of the hub.

The blood collection set may further include a length of flexible tubing having opposed proximal and distal ends. The distal end of the flexible tubing may be connected to the proximal end of the hub such that the lumen through the needle cannula and the passage through the hub both communicate with the passage through the flexible tubing. The flexible tubing further includes a proximal end that may be connected to a fitting. The fitting may comprise a needle cannula that enables the blood collection set to be placed in communication with a reservoir for receiving a sample of blood. The tubing and the fitting may be of conventional design.

The blood collection set may further include a substantially rigid generally tubular safety cap mounted over the needle cannula for protection against accidental needle sticks prior to use of the blood collection set. The safety cap may include a proximal end that is frictionally engaged with the hub. The rigid tubular safety cap may be removed immediately prior to use of the blood collection set.

The blood collection set further includes a safety shield that is telescoped within the outer tube of the hub and telescoped over the inner tube of the hub and cannula. Thus, the shield can be moved from a proximal position, where the needle cannula is exposed, to a distal position, where the needle cannula is safely shielded. Biasing means are provided between the shield and the hub for urging the shield to the distal position. The biasing means may be a coil spring that surrounds a portion of the hub.

The blood collection set further comprises a retainer for releasably retaining the shield in the proximal position relative to the hub and the needle cannula and against the stored energy of the biasing means. The retainer may define a resiliently deflectable actuating finger that projects into the aperture in the outer tube of the hub. The end of the actuating finger may be depressed to separate the actuating finger from the aperture and enable the shield to be propelled toward the distal position in response to forces exerted by the biasing means.

DETAILED DESCRIPTION

Figure 1:
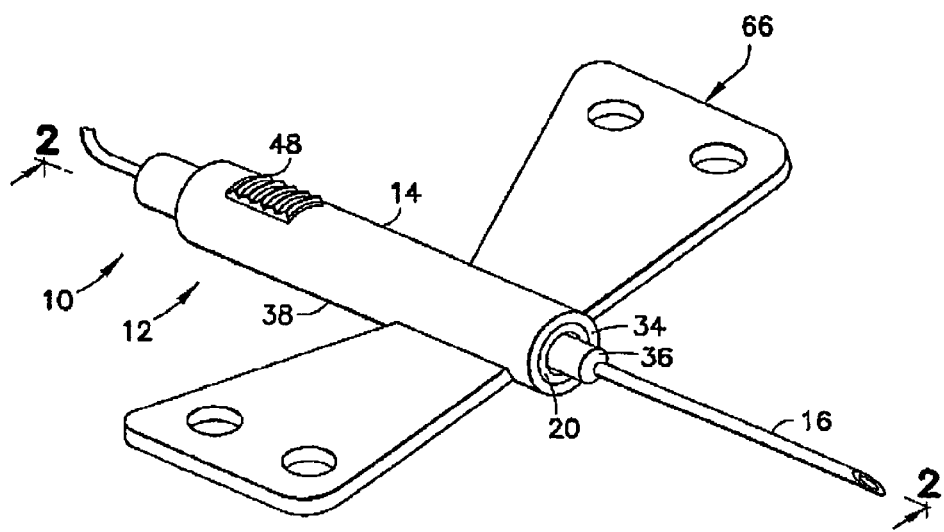
FIG. 1 is a perspective view of a blood collection set in accordance with the subject invention with the needle exposed.
Figure 2:
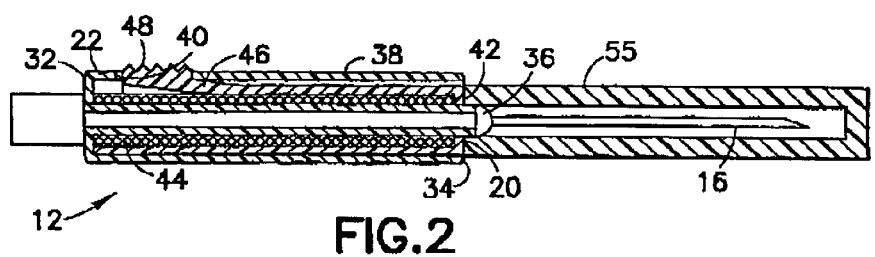
FIG. 2 is a cross-sectional view taken along line 2—2 in FIG. 1.
Figure 3:
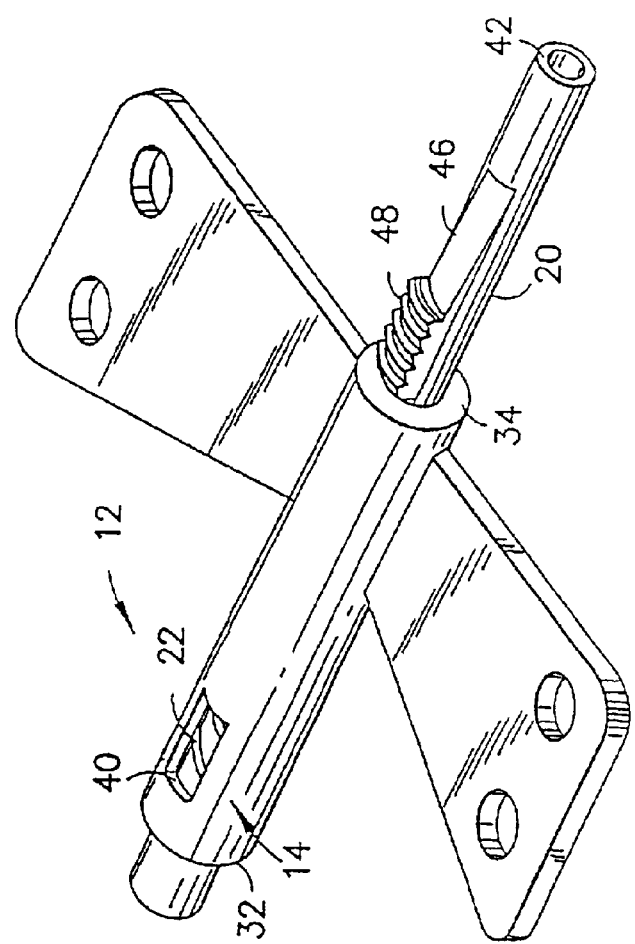
FIG. 3 is a perspective view similar to FIG. 1, but showing the needle of the blood collection set in the shielded condition.

A blood collection set in accordance with the subject invention is identified generally by the numeral 10 in FIGS. 1–3. Blood collection set 10 includes a needle assembly 12 which comprises a needle hub 14, a needle cannula 16, a safety cap 55, a shield 20 and a spring 22. Hub 14 includes a proximal end 32 and a distal end 34. A tubular inner wall 36 extends from proximal end 32 to distal end 34 and is connected to needle cannula 16 as in the prior embodiments. A tubular outer wall 38 is disposed in concentric spaced relationship around tubular inner wall 36. Tubular outer wall 38 is formed with a retention aperture 40 extending therethrough at a location near proximal end 32. Wings 66 extend transversely from tubular outer wall as in the prior embodiments.

Shield 20 is telescoped between inner and outer walls 36 and 38 of hub 14 and includes a proximal end 42 and a distal end 44. A resiliently deflectable finger 46 projects proximally and outwardly from a location between proximal and distal ends 42 and 44. Finger 46 includes an actuator 48 that is releasably engaged in retention aperture 40 of outer wall 38 on hub 14. Spring 22 is captured in a compressed condition between proximal end 32 of hub 14 and shield 20.

Needle assembly 12 is used in the conventional manner. After withdrawal of needle cannula 16 from the patient, shield 20 is activated merely by exerting a pressing force on actuator 48. This pressing force will disengage actuator 48 from aperture 40 and shield 20 will be propelled distally into surrounding shielding disposition relative to needle cannula 16. After sufficient distal movement, resiliently deflectable finger 46 will pass beyond distal end 34 of hub 14 and will resiliently move into a position aligned with portions of outer wall 38 at distal end 34. Thus, re-exposure of needle cannula is substantially prevented. On the other hand, engagement between an inwardly directed flange at distal end 34 of hub 14 and an outwardly directed flange on shield 20 prevents complete separation of shield 20 from hub 14.

What is claimed is:

1. A needle assembly for a blood collection set comprising:
   a hub having an inner tube and an outer tube surrounding said inner tube, each said tube of said hub having a proximal end and a distal end, said proximal ends of said inner and outer tubes being connected, said distal ends of said inner and outer tubes of said hub being spaced from one another such that a cylindrical space is defined between distal portions of said inner and outer tubes, said outer tube of said hub including a retaining aperture extending therethrough and into communication with said space;
   a needle cannula having a proximal end rigidly connected to said distal end of said inner tube of said hub;
   a shield telescoped within said cylindrical space of said hub and movable from a proximal position where said needle cannula is exposed to a distal position where said needle cannula is shielded, said shield comprising a resiliently deflectable finger projecting proximally and outwardly, said finger including an actuator engaging in said retaining aperture of said outer tube of said hub for retaining said shield in said proximal position;
   a spring disposed between the shield and the hub for urging said shield to said distal position, whereby inwardly directed forces on said actuator displaces said actuator from said retaining aperture of said outer tube and enables said spring to propel said shield to said distal position,
   wherein in the initial state of the assembly prior to use, said cannula is exposed, said shield is located in said proximal position, and said assembly further comprises a safety cap disposed over at least a portion of the exposed needle cannula.

2. The needle assembly of claim 1, wherein said resiliently deflectable finger comprises a proximal face dimensioned for engaging said outer tube at said distal end of said hub when said shield is in said distal position for preventing proximal movement of said shield relative to said hub.

3. The needle assembly of claim 1, wherein the outer tube of the hub includes a pair of resiliently deflectable radially extending wings for gripping and securing said needle assembly.

4. The needle assembly of claim 1, wherein the hub includes a proximal wall for connecting said inner and outer tubes, said spring comprising a coil spring having a proximal end engaged against the proximal wall of the hub and a distal end engaged against the shield.

5. The needle assembly of claim 4, wherein the shield has opposite proximal and distal ends, the distal end of the shield comprising an annular distal end wall extending inwardly for sliding contact with the inner tube of the hub portions of the shield between the annular distal end wall and the proximal end of the shield being spaced radially outwardly from the inner tube of the hub, the distal end of the spring engaging the annular distal end wall of the shield, such that portions of said spring are disposed between said shield and said inner tube of said hub.

6. The needle assembly of claim 1, further comprising a flexible tube connected to the proximal end of the hub such that a passage through said tube communicates with the passage through the inner wall of the hub.

* * * * *